United States Patent
Knauf et al.

[11] Patent Number: 5,885,598
[45] Date of Patent: Mar. 23, 1999

[54] INSECT CONTROL COMPOSITIONS COMPRISING ENTOMOPATHOGENIC FUNGI

[75] Inventors: Werner Knauf, Eppstein, Germany; Esperanza Morales, Bogota, Colombia

[73] Assignee: Hoechst Schering Agr Evo GmbH, Berlin, Germany

[21] Appl. No.: 513,609

[22] Filed: Aug. 10, 1995

[30] Foreign Application Priority Data

Aug. 16, 1994 [DE] Germany ............ 44 28 981.2

[51] Int. Cl.⁶ ............ A01N 25/32; A01N 63/04
[52] U.S. Cl. ............ 424/405; 424/406; 424/407; 424/408; 424/409; 424/417; 424/418; 424/419; 424/420; 424/421; 424/93.5; 574/223.8
[58] Field of Search ............ 514/223.8; 424/405–410, 424/417–421, 93.5

[56] References Cited

U.S. PATENT DOCUMENTS 5,631,276  5/1997  Kern ........................... 514/431

OTHER PUBLICATIONS

Soper et al., *Environmental Entymology*, vol. 3, pp. 560–562, 1974.
Borisov and Akhatov, *Zashcita Rastenii*, No. 9, pp. 6–10, (1991).
H. Borner, Plant Diseases and Plant Protection, 1983, pp. 288–349.
H. Schmutterer, Pests of Crops in Northeast and Central Africa, 1969.
G. Fröhlich, Plant Protection in the Tropics, 1974.
B.S. Ekbohm, J. Agric, Res., vol. 9, 1979, pp. 229–268.
Gisbert Zimmermann, Pest Science, vol. 37, 1993, pp. 375–379.
A.T. Gillespie, BCPC Mono, Biotechnology & Crop Improvement & Protection, vol. 34, 1986, pp. 237–243.
H. Kanno, Br. Crop, Prot. Conf.–Pests Dis., vol. 1, 1981, pp. 59–67.
M. Shibuya, Japan Pesticides Information, vol. 44, 1984, pp. 16–21.
A. Bassi, C.R. Acad. Sci. Paris, vol. 2, pp. 434–437.
V.H. Domsch, Compendium of Soil Fungi, vol. 190, No. 1, pp. 136–139.
R.A. Samson, Atlas of Entomopathogenic Fungi, 1988.
Thang et al, 19. Pest Control Council of The Philippines Cebu City 3–7 May 1988.

*Primary Examiner*—Neil S. Levy
*Attorney, Agent, or Firm*—Frommer Lawrence & Haug LLP

[57] ABSTRACT

Insecticidal compositions which have an active content of buprofezin (I)

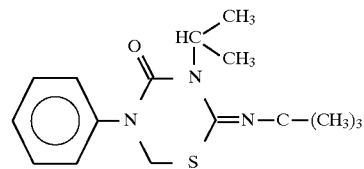

in combination with insect-pathogenic fungi.

15 Claims, No Drawings

INSECT CONTROL COMPOSITIONS COMPRISING ENTOMOPATHOGENIC FUNGI

In the cultivation of crop plants it is necessary to control numerous types of pests, for example scale insects, thrips, whitefly or leafhoppers (H. Börner, Pflanzenkrankheiten und Pflanzenschutz [Plant diseases and plant protection], UTB Ulmer Verlag, 1983, 406 pp.; H. Schmutterer, Pests of Crops in Northeast and Central Africa, G. Fischer Verlag, 1969, 296 pp.; G. Fröhlich, Pflanzenschutz in den Tropen [Plant protection in the tropics], Verlag Harri Deutsch, 1974, 525 pp.).

The pests are controlled using insecticides which, in most cases, possess only one mechanism of action, a fact which fairly rapidly promotes the development of resistance. This selection of resistant strains may lead to a situation in which the cultivation of crop plants becomes completely impossible in some regions.

One possibility for overcoming such difficulties is to alternate the active compounds used, so that the development of resistance can be prevented or at least slowed down. However, this requires the continual development of new active compounds, so as to avoid selection to the particular mechanism of action.

In contrast, it is more sensible to be able to employ an active compound which has proven sufficiently effective for as long as possible, especially when it has shown itself to be environmentally compatible to a particularly high degree and to possess only minimal side-effects.

An example of one such active compound is buprofezin. This insecticide has a particular mechanism of action: it acts as a molting inhibitor, and thus appears particularly suitable for the control of scale insects, whitefly and leafhoppers.

Buprofezin, however, has a number of disadvantages. One of these, for example, is that the active compound is not sufficiently effective against thrips. And thrips in particular is encountered very often together with whitefly, so that the two species have to be controlled separately with different active compounds. Furthermore, buprofezin is only effective at the actual time when the insect to be treated is molting (since it is a molting inhibitor). Therefore, it is largely without effect against imagines, which are thus still capable of ovi-position, so that when the covering of active compound on the surface of the plant has disappeared the insect is able to repopulate.

Recently, certain biological insecticides (biologicals) based on microorganisms have shown that they are also able to control sucking insects. This is described in various publications; see, for example, Ekbohm, B. S., Investigation on the Potential of a Parasitic Fungus (*Verticillium lecanii*) for Biological Control of the Greenhouse Whitefly (*Trialeurodes vaporariorum*) Swedish J. agric. Res. 9, 1979, pp. 129 to 138; Zimmermann, G., The entomopathogenic Fungus *Metarhizium anisopliae* and its Potential as a Biocontrol Agent, Pest. Sci. 37, 1993, pp. 375 to 379; Gilksie, A. T., The Potential of Entomogenous Fungi as Control Agents for Onion Thrips, Thrips tabaci, BCPC Mono. No. 34 Biotechnology and Crop Improvement and Protection, 1986, pp. 237 to 243.

In this context, particular mention should be made of the insect-pathogenic fungi from the genera Hirsutella, Verticillium, Metarhizium, Beauveria, Paecilomyces, Nemouraea, etc, which develop a certain effect but only at comparatively high dosages lead to the desired success in control. Control of the abovementioned sucking insects with these mycoinsecticides alone is therefore in many cases uneconomic or not sufficiently reliable.

Surprisingly it has now been found that the compound buprofezin and spores or particles of insect-pathogenic fungi, when used together, exhibit an extremely good activity against a broad spectrum of different insects.

In this way it is possible to employ buprofezin without the known disadvantages and, by means of the second mechanism of action introduced by using the mixture, to achieve a long residence time in the areas where it is applied without having to be concerned about the development of resistance. At the same time, the mycoinsecticides mentioned can be employed at considerably lower rates, so that their use lies within the economic range.

Furthermore, in the case of thrips too, the action of the mycoinsecticide advantageously widens the scope of action of the combination, in comparison with the use of the active compound alone.

This advantageous combined use of mycoinsecticides and a molting inhibitor against sucking insects has not been disclosed beforehand and is the objective of the present invention.

The present invention provides insecticidal compositions which comprise an active content of buprofezin (compound of formula I, component A)

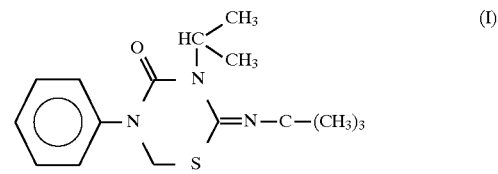

in combination with at least one insect-pathogenic fungus (component B).

In the text below, the term active compound is also used for each of the two components A and B.

Buprofezin is described by H. Kanno and K. Ikeda in Proc. Br. Crop. Prot. Conf.—Pests Dis. 1981, 1, p. 59 ff. Its chemical name is 2-tert-butylimino-3-isopropyl-5-phenyl-3,4,5,6-tetrahydro-2H-1,3,5-thiadiazin-4-one.

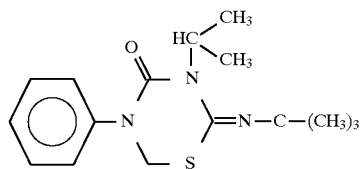

Its biological properties are described in M. Shibuya, Japan Pesticides Information No. 44, 1984, p. 17 ff.

Of particular interest in its action against insects is a mixture of buprofezin and fungi of the genera Hirsutella, Verticillium, Metarhizium, Beauveria, Paecilomyces or Nemouraea. In this case, the mycoinsecticides may be present in various forms: as conidiospores, as blastospores, as hyphal assemblies, as hyphal fragments or as a mixture of two or more of the forms mentioned.

A particularly preferred mycoinsecticide is the fungus Beauveria bassiana, which has been described by Bassi, A. (1836, C.R. Acad. Sci. Paris 2, 434 to 436), Domsch, V. H. et al. (190, Compendium of Soil Fungi 1, 136 to 139) and Samson, R. A. et al. (1988, Atlas of Entomopathogenic Fungi, Springer-Verlag, Berlin). It is available from Mycotech (Butte, Mont., USA), Hoechst Schering AgrEvo GmbH, and the Fermone Corp. (Phoenix, Ariz., USA).

Both active compound components may be formulated separately or in a conjoint formulation, for example as a dust, wettable powder, spray granules, extruder granules, oil, emulsifiable concentrate, water-dispersible granules (WG), which formulations may also contain additional auxiliaries, UV stabilizers or other protective substances (such as antioxidants), dispersion auxiliaries, adhesion agents, fillers, organic and inorganic carriers, colorants, oils, inorganic and organic salts and nutrients, emulsifiers or other surface-active substances.

The fungi used are composed of strains which are specifically effective against the species to be controlled, or of mixtures thereof, and can have been produced either from surface cultures or, alternatively, from submerged cultures.

The ratios in which the two components are mixed may vary within broad limits. They depend, in particular, on the co-component employed, on the development stage of the tests and on the climatic conditions.

Mixtures which have been found to be effective are those in which the content of buprofezin is between 0.01 and 50%, preferably from 0.1 to 50%, and the proportion of mycoinsecticide is from $10^2$ to $10^{15}$ spores, preferably from $10^5$ to $10^{12}$ spores, or from 0.01 to 0.5 g of mycelium material per gram of formulated substance.

The active compound combinations according to the invention may be either in the form of mixed formulations of the two components, which are then, in a conventional manner, diluted with water or employed as granules, or may be produced as so-called tank mixes by conjoint dilution of the separately formulated components with water.

The invention also provides compositions which comprise the two components A and B in addition to suitable formulation auxiliaries. The components may also be formulated in a variety of ways depending on the prevailing biological and/or physicochemical parameters.

Examples of suitable formulation options are: yeast formulations, starch formulations, wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dusts (DP), dressing agents, granules for soil application or for broadcasting, or water-dispersible granules (WG), ULV formulations, microcapsules and baits (substrates).

Formulations which are of particular interest are oil-in-water and water-in-oil emulsions, wettable powders or granules.

These individual formulation types are known in principle and are described, for example, in: Winnacker-Küchler, "Chemische Technologie" [Chemical technology], Volume 7, C. Hauser Verlag, Munich, 4th ed. 1986; van Valkenburg, "Pesticides Formulations", Marcel Dekker N.Y., 2nd edition 1972–73; K. Martens, "Spray Drying Handbook", 3rd edition, G. Goodwin Ltd., London.

The necessary formulation auxiliaries, such as inert materials, surfactants, solvents and other additives, are also known and are described, for example, in: "Handbook of Insecticide Dust Diluents and Carriers", 2nd edition, Darland Books, Caldwell N.J.; H. v. Olphen, "Introduction to Clay Colloid Chemistry", 2nd edition, J. Wiley Sons, N.Y., Marsden, "Solvents Guide", 2nd edition, Interscience, N.Y. 1950; McCutcheon's, "Detergents and Emulsifiers Annual", MC Publ. Gorp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag, Munich, 4th ed. 1986.

On the basis of these formulations it is also possible to produce combinations with further pesticidal substances, such as selective herbicides, specific fungicides or insecticides, and fertilizers and/or growth regulators, for example in the form of a ready-to-use formulation or as a tank mix.

Wettable powders are preparations, uniformly dispersible in water, which comprise, in addition to the active compound and besides a diluent or inert material, wetting agents, for example polyethoxylated alkylphenols, polyethoxylated fatty alcohols or fatty amines, alkane- or alkylbenzene-sulfonates and dispersants, for example sodium ligninsulfonate, sodium 2,2'-dinaphthylmethane-6,6'-disulfonate, sodium dibutylnaphthalenesulfonates, or sodium oleylmethyltaurinate.

Emulsifiable concentrates are prepared by dissolving the active compound in an organic solvent, for example butanol, cyclohexanone, dimethylformamide, xylene or else higher-boiling aromatics or hydrocarbons, with addition of one or more emulsifiers. Examples of emulsifiers which can be used are: calcium salts of alkylarylsulfonic acid, such as Ca dodecylbenzenesulfonate, or nonionic emulsifiers such as fatty acid polyglycol esters, alkyl-aryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite and pyrophyllite or diatomaceous earth.

Granules can be prepared either by atomizing the active compound onto adsorptive, granulated inert material or by applying active compound concentrates to the surface of carrier materials such sand, kaolinites or granulated inert material by means of adhesives, for example polyvinyl alcohol, sodium polyacrylate, or alternatively mineral oils. Suitable active compounds can also be prepared in the manner conventional for the preparation of fertilizer granules, if desired as a mixture with fertilizers.

The agrochemical formulations generally contain from 0.1 to 99% by weight, in particular from 2 to 95% by weight, of the two components A and B. The concentrations of the active compounds A and B in the formulations may be different.

In wettable powders, the concentration of active compound is, for example, from about 10 to 95% by weight, the remainder to 100% by weight consisting of conventional formulation components. In the case of emulsifiable concentrates, the concentration of active compound may be from about 1 to 85% by weight, preferably from 5 to 80% by weight. Formulations in dust form contain from about 1 to 25% by weight, preferably from 5 to 20% by weight of active compound, while sprayable solutions contain from about 0.2 to 25% by weight, preferably from 2 to 20% by weight of active compound.

The content of active compound in granules, e.g. water-dispersible granules, is partly dependent on whether the active compound is a liquid or a solid and on which granulation auxiliaries and fillers are used. In general, the content in the case of water-dispersible granules is between 5 and 90% by weight, whereas in granules for broadcasting it is between 1 and 50%, preferably between 2 and 25%.

In addition, the abovementioned formulations of active compound may comprise the adhesives, wetting agents, dispersants, emulsifiers, penetration agents, solvents, fillers or carriers which are conventional in each particular case.

For application, the formulations in their conventional commercial form are diluted, if desired, in a conventional manner, for example using water in the case of wettable powders, emulsifiable concentrates, dispersions and water-dispersible granules. Dust formulations, soil granules and granules for broadcasting, as well as sprayable solutions, are not usually diluted any further with additional inert materials prior to their application.

Component B can be formulated, for example, as described by Prior, C. et al. in the Journal of Invertebrate Pathology 52 (1988), 66 to 72. Component B is preferably formulated as proposed in P 4404702.9.

The required application rate for the mixture varies with the external conditions, such as temperature, humidity, etc.

The two components A and B may be applied simultaneously or in succession. The invention additionally provides a method in which the compositions according to the invention are applied in succession. The interval between the individual applications should be not more than 14 days, and is preferably from 2 to 7 days, especially from 3 to 5 days.

The second application should sensibly be made after the first application to the plant has dried, so as to avoid the first component being washed off in an unwanted fashion.

The combination of the two components, buprofezin and the fungi (B), couples good tolerance by plants and favorable toxicity to warm-blooded animals with suitability for the control of animal pests, especially insects, which are encountered in agriculture.

The synergistic mixture of the two components is active against normally sensitive and resistant strains and against individual development stages. The compositions of the invention possess an outstanding insecticidal activity against a broad spectrum of economically important pests. Some specific examples of the pests which can be controlled by the compositions according to the invention will be given below, without any intention thereby to limit the invention to particular species.

The combination has proven particularly effective with the following organisms: species from the order of the Thysanoptera (thrips), especially the genera Haplothrips (e.g. *H. aculeatus*), Thrips (e.g. *T. oryzae, T. tabaci, T. occidentalis, T. californicus,* etc.) and of the genus Scirtothrips (e.g. *S. aurantii, S. citri*) and other species from the said order.

From the suborder of the Homoptera (plant sap feeders), species from the family of the Cicadidae (leafhoppers) such as, for example, *Sogatella furcifera, Nephotettix apicalis, Nephotettix impicticeps, Nephotettix cincticeps, Nilaparvata lugens,* and other species from this suborder.

From the family of the Coccidae (scale insects) species of the genera Orthezia (e.g. *O. insignia*); Icerya (e.g. *I. aegyptica, I. purchasi*); Pseudococcus (e.g. *P. citri, P. adonidum, P. comstocki; P. gahani; P. maritimus*); Dysmicoccus (e.g. *D. brevipes*); Coccus (*C. hesperidum*); Eulecanium (e.g. *E. corni; E. persicae*); Saissetia (e.g. *S. coffeae; S. nigra; S. oleae*); Aspidiotus (e.g. *A. destructor; A. hederae;* Chrysomphalus (e.g. *C. dictyospermi; C. ficus*); Aonidiella (e.g. *A. aurantii; A. citrina*); Quadraspidiotus (e.g. *Q. perniciosus*); Lepidosaphes (e.g. *L. beckii*) and other species from this family.

Species from the family of the Aleurodidae (whitefly) such as, for example, *Trialeurodes vaporariorum, T. abulilonea, T. floridensis, T. variabilis, Bemisia tabaci* and other species from this family.

With the active compound combinations according to the invention, an insecticidal activity is obtained which goes beyond that which might be expected on the basis of the action of the individual components. These increases in activity make it possible to reduce considerably the quantities in which the individual active compounds are employed. The combination of the active compounds may also improve their long-term action or may accelerate the speed of action. Such properties offer the user considerable advantages in the practical control of insects. Insects can be controlled at lower expense, more quickly, less labor-intensively and more permanently, and it is thereby possible to get a greater yield from a stock of crop plants.

The following examples serve to illustrate the invention without limiting it to said examples:

A. Biological examples

In each case, the calculated degree of activity was compared with that found by experiment with the combinations.

If the actual damage is greater than that anticipated by calculation, then the action of the combination is super-additive, i.e. there is a synergistic effect on action. The active compound combinations according to the invention have an insecticidal action which is higher than is to be expected on the basis of the observed actions of the individual components when employed alone. The active compound combinations are therefore synergistic.

EXAMPLE 1

*Trialeurodes vaporariorum* (whitefly)

Conidiospores of *Beauveria bassiana* were harvested from agar cultures. The age of the spores was between 1 and 6 days. These spores were diluted in a mixture of water and 0.05% Tween 80 to give a density of $10^{10}$ spores per ml. The number of spores was determined using a Neubauer chamber.

Colonies of *T. vaporariorum* were cultured on bean leaves until the larvae had reached a stage 3-4.

The larvae were placed on fresh bean leaves, and the leaves were sprayed with the active compounds or mixtures thereof at various concentrations.

After treatment, the plants were covered with a transparent plastic container and incubated at 28° C. and an atmospheric humidity of $\geq 80\%$ for 7 days.

After this 7-day period, the leaves of the control plants were compared with those of the treated plants for the different quantities of mature or emerged flies (empty larval sheaths) and dead animals.

Buprofezin was used in an aqueous solution (WP50) at 8, 4, 2 and 1 ppm ($\triangleq$ mg/liter).

The following batches were tested:
1. Control
2. *B. bassiana* ($10^{10}$ spores/ml)
3. Buprofezin 8–1 ppm (a.i.)
4. Buprofezin+B. bassiana It is evident from the table that markedly better results were obtained using the combinations.

| Active compound/component | Application | % action/mortality |
|---|---|---|
| 1. Control | Water | 3 |
| 2. *B. bassiana* | $10^{10}$ spores/ml | 23.5 |
| 3. Buprofezin | 8 mg/l | 63.5 |
| | 4 " | 18.0 |
| | 2 " | 2.3 |
| | 1 " | 4.7 |
| 4. *B. bassiana* | $10^{10}$ spores/ml | |
| + buprofezin | +8 mg/l | 100 |
| | +4 " | 89.4 |
| | +2 " | 65.8 |
| | +1 " | 52.5 |

We claim:
1. An insecticidal composition which comprises synergistic effect amounts of buprofezin (A) and at least one mycoinsecticide (B), and wherein the concentration of buprofezin is more than 5.5 ppm.

2. The composition as claimed in claim 1, in which the mycoinsecticide is selected from the group consisting of the genera Hirsutella, Verticillium, Metarhizium, Beauveria, Paecilomyces and Nemouraea.

3. The composition as claimed in claim 1, in which *Beauveria bassiana* is the mycoinsecticide.

4. The composition as claimed in claim 1, in which the mycoinsecticide is obtained from a submerged culture or from a surface culture.

5. The composition as claimed in claim 1, in which the mycoinsecticide is selected from the group consisting of conidiospores and blastospores.

6. The composition as claimed in claim 1, in which the mycoinsecticide comprises mycelium or mycelial fragments.

7. The composition as claimed in claim 1, which comprises from 1 to 99% by weight of buprofezin and mycoinsecticide.

8. The composition as claimed in claim 1, which is formulated in a conventional crop protection product formulation selected from the group consisting of wettable powders, emulsifiable concentrates, aqueous solutions, emulsions, sprayable solutions (tank mix), oil-and-water-based dispersions, suspoemulsions, dusts, dressing agents, soil granules or granules for broadcasting, coated material, water-dispersible and water, emulsifiable granules, ultralow volume formulations, microcapsules, silica gela, polymer gels, Saccaromyces, bacteria and waxes.

9. A method of controlling insect pests, which comprises applying a synergistic effective amount of an insecticidal composition as claimed in claim 1, to these pests or to the plants, areas or substrates infested with the pests.

10. The method of controlling insect pests, which comprises applying a synergistic effective amount of the composition formulated as claimed in claim 8, to these pests or to the plants, areas or substrates infested with the pests.

11. A process for the preparation of a formulation comprising the composition as claimed in claim 1, comprises formulating the composition in a conventional plant protection formulation selected from the group consisting of wettable powders, emulsifiable concentrates, aqueous solutions, emulsions, sprayable solutions (tank mix), oil-and-water-based dispersions, suspoemulsions, dusts, dressing agents, soil granules or granules for broadcasting, coated material, water-dispersible and water, emulsifiable granules, ultralow volume formulations, microcapsules, silica gela, polymer gels, Saccaromyces, bacteria and waxes.

12. The method as claimed in claim 9, wherein the plants are vegetables or ornamentals which are cultivated under glass.

13. The method as claimed in claim 9, wherein the plants are selected from the group consisting of cotton, soybean, rice and coffee.

14. A method of controlling insect pests which comprises applying synergistic effect amounts of components A and B of the composition of claim 1, in succession, at an interval of from 2 to 14 days.

15. A method of controlling insect pests which comprises applying synergistic effect amounts of the components B and A of the composition of claim 1, in succession, at an interval of from 2 to 14 days.

* * * * *